(12) United States Patent
Kuei et al.

(10) Patent No.: US 8,299,028 B2
(45) Date of Patent: Oct. 30, 2012

(54) CHIMERIC PEPTIDE ANTAGONIST FOR GPCR135 OR GPCR142

(75) Inventors: Chester Kuei, San Diego, CA (US); Changlu Liu, San Diego, CA (US); Cindy M. Pudiak, Binghamton, NY (US); Jonathan Edward Shelton, San Marcos, CA (US); Steven W. Sutton, Carlsbad, CA (US)

(73) Assignee: Janssen Pharmaceutica NV, Beerse (BE)

( * ) Notice: Subject to any disclaimer, the term of this patent is extended or adjusted under 35 U.S.C. 154(b) by 180 days.

(21) Appl. No.: 12/449,137

(22) PCT Filed: Jan. 23, 2008

(86) PCT No.: PCT/US2008/000917
§ 371 (c)(1), (2), (4) Date: Jan. 25, 2010

(87) PCT Pub. No.: WO2008/094437
PCT Pub. Date: Aug. 7, 2008

(65) Prior Publication Data
US 2010/0145007 A1  Jun. 10, 2010

Related U.S. Application Data

(60) Provisional application No. 60/898,693, filed on Jan. 30, 2007.

(51) Int. Cl.
*A61K 38/22* (2006.01)
*C07K 14/64* (2006.01)
(52) U.S. Cl. .............. 514/12.7; 514/20.6; 514/21.3
(58) Field of Classification Search .......... None
See application file for complete search history.

(56) References Cited

FOREIGN PATENT DOCUMENTS

| WO | WO01/68862 | 9/2001 |
|---|---|---|
| WO | WO02/00719 | 1/2002 |
| WO | WO2004/082598 | 9/2004 |
| WO | WO2004/113381 | 12/2004 |
| WO | WO2005/004807 | 1/2005 |
| WO | WO2005/014616 | 2/2005 |
| WO | WO2006/026355 | 3/2006 |
| WO | WO2007/117400 | 10/2007 |

OTHER PUBLICATIONS

Bathgate et al.,"Human Relaxin Gene 3 (H3) and the Equivalent Mouse Relaxin (M3) Gene", 2002, J. Biol. Chem., 277(2):1148-1157.
Boels et al., "Identification of a mouse orthologue of the G-protein-coupled receptor SALPR and its expression in adult mouse brain and during development", 2004, Dev. Brain Res., 152:265-268.
Burazin etal., "Restricted, but abundant, expression of the novel rat gene-3 (R3) relaxin in the dorsal tegmental region of brain", 2002, J. Neurochem., 82:1553-1557.
Chen et al., "Pharmacological Characterization of Relaxin-3/INSL7 Receptors GPCR135 and GPCR142 from Different Mammalian Species", 2005, J. Pharmacol. Exp. Ther., 312(1):83-95.
Civelli et al., "Novel Neurotransmitters as Natural Ligands of Orphan G-protein-coupled Receptors", 2001, Trends Neurosci., 24(4):230-237.
Conklin et al. "Identification of INSL5, a New Member of the Insulin Superfamily", 1999, Genomics, 60(1):50-56.
Goto et al., "Connections of the Nucleus Incertus", 2001, J. Comp. Neurol., 438:86-122.
Hida et al., "Chronic Intracerebroventricular Administration of Relaxin-3 Increases Body Weight in Rats", 2006, J. Recep. and Signal Transduction, 26:147-158.
Hosaka et al., "Arg-X-Lys/Arg-Arg Motif as a Signal for Precursor Cleavage Catalyzed by Furin with the Consititutive Secretory Pathway", 1991, J. Biol. Chem., 266(19):12127-12130.
Howard et al., "Orphan G-protein-coupled receptors and natural ligand discovery", 2001, Trends in Pharmacological Sciences, 22(3):132-140.
Hsu et al., "The Three Subfamilies of Leucine-Rich Repeat-Containing G Protein-Coupled Receptors (LGR): Identification of LGR6 and LGR7 and the Signaling Mechanism for LGR7", 2000, Mol. Endocrinol., 14(8):1257-1271.
Hsu et al., "Activation of Orphan Receptors by the Hormone Relaxin", 2002, Science, 295:671-674.
Hudson et al., "Structure of a Genomic Clone Encoding Biologically Active Human Relaxin", 1983, Nature, 301:628-631.
Hudson et al., "Relaxin gene expression in human ovaries and the predicted structure of a human preprorelaxin by analysis of cDNA clones", 1984, EMBO J., 3(10):2333-2339.
Krajnc-Franken et al., "Impaired Nipple Development and Parturition in LGR7 Knockout Mice",2004, Mol. Cell Biol., 24 (2):687-696.
Kuei et al., "R3(B[Delta]23-27)R/I5 Chimeric Peptide, a Selective Antagonist for GPCR135 and GPCR142 over Relaxin Receptor LGR7", 2007, J. Biol. Chem., 282(35):25425-25435.
Liu et al., "Identification of Relaxin-3/INSL7 as an Endogenous Ligand for the Orphan G-protein-coupled Receptor GPCR135", 2003, J. Biol. Chem., 278(5):50754-50764.
Liu et al., "Identification of Relaxin-3/INSL7 as a Ligand for GPCR142", 2003, J. Biol. Chem., 278(50):50765-50770.
Liu et al., "INSL5 is a High Affinity Specific Agonist for GPCR142 (GPR100)", 2005, J. Biol. Chem., 280(1):292-300.
Liu et al., "Relaxin-3/Insulin-Like Peptide 5 Chimeric Peptide, a Selective Ligand for G Protein-Coupled Receptor (GPCR)135 and GPCR142 over Leucine-Rich Repeat-Containing G Protein-Coupled Receptor 7", 2005, Mol. Pharmacol., 67(1):231-240.
Ma et al., "Relaxin-3 in Gaba Projection Neurons of Nucleus Incertus Suggests Widespread Influence on Forebrain Circuits via G-Protein-Coupled Receptor-135 in the Rat", 2007, Neuroscience, 144:165-190.
Matsumoto et al.,"The novel G-protein coupled receptor SALPR shares sequence similarity with somatostatin and angiotensin receptors ", 2000, Gene, 248:183-189.
McGowan et al., "Central Relaxin-3 Administration Causes Hyperphagia in Male Wistar Rats", 2005, Endocrinology, 146(8):3295-3300.
Nistri et al., "Relaxin in Vascular Physiology and Pathophysiology: Possible Implications in Ischemic Brain Disease", 2005, Curr. Neurovasc. Res., 2:225-233.

(Continued)

*Primary Examiner* — Robert Landsman
*Assistant Examiner* — Ian Dang

(57) ABSTRACT

The chimeric polypeptide R3(BΔ23-27)R/I5 is described, which is a high-affinity antagonist for GPCR135 and GPCR142 over LGR7.

3 Claims, 7 Drawing Sheets

OTHER PUBLICATIONS

Potter et al., "Distribution of corticotropin-releasing factor receptor mRNA expression in the rat brain and pituitary", 1994, Proc. Natl. Acad. Sci. USA, 91:8777-8781.

Sherwood, "Relaxin's physiological roles and other diverse actions", 2004, Endocrine Reviews, 25(2):205-234.

Sudo et al., "H3 Relaxin Is a Specific Ligand for LGR7 and Activates the Receptor by Interacting with Both the Ectodomain and the Exoloop 2", 2003, J. Biol. Chem., 278(10):7855-7862.

Sutton et al., "Distribution of G-Protein-Coupled Receptor (GPCR)135 Binding Sites and Receptor mRNA in the Rat Brain Suggests a Role for Relaxin-3 in Neuroendocrine Sensory Processing", 2004, Neuroendocrinology 80:298-307.

Sutton et al., "G-Protein-Coupled Receptor (GPCR)-142 Does Not Contribute to Relaxin-3 Binding in the Mouse Brain: Further Support that Relaxin-3 is the Physiological Ligand for GPCR135", 2005, Neuroendocrinology, 82:139-150.

Tan et al., "Quantitative autoradiographic studies of relaxin binding in rat atria, uterus and cerebral cortex: characterization and effects of oestrogen treatment", 1999, Br. J. Pharmacol., 127:91-98.

Tanaka et al., "Neurons Expressing Relaxin 3/INSL 7 in the Nucleus Incertus Respond to Stress", 2005, Eur. J. Neurosci., 21:1659-1670.

Thornton et al., "The Effects of Centrally Administered Porcine Relaxin on Drinking Behaviour in Male and Female Rats", 1995, J. Neuroendocrinol., 7:165-169.

Wilson et al., "Orphan G-protein-coupled receptors: the next generation of drug targets?", 1998, Brit. J. Pharm, 125:1387-1392.

Wilson et al., "Relaxin-induced reduction of infarct size in male rats receiving MCAO is dependent on nitric oxide synthesis and not estrogenic mechanisms", 2006, Neurosci. Lett., 393:160-164.

Zhao et al., "Mice without a Functional Relaxin Gene Are Unable to Deliver Milk to their Pups", 1999, Endocrinology 140(1):445-453.

Figure 7

B-chain

| | | |
|---|---|---|
| (SEQ ID NO:20) | Relaxin-1: | KWKDDVIKLCGRELVRAQIAICGMSTWS |
| (SEQ ID NO:21) | Relaxin-2: | DSWMEEVIKLCGRELVRAQIAICGMSTWS |
| (SEQ ID NO:12) | Relaxin-3: | RAAPYGVRLCGREFIRAVIFTCGGSRW |
| (SEQ ID NO:22) | INSL3: | PTPEMREKLCGHHFVRALVRVCGGPRWSTEA |
| (SEQ ID NO:23) | INSL4: | ESLAAELRGCGPRFGKHLLSYCPMPEK |
| (SEQ ID NO:24) | INSL5: | KESVRLCGLEYIRTVIYICASSRW |
| (SEQ ID NO:25) | INSL6: | ISSARKLCGRYLVKEIEKLCGHANWSQF |
| (SEQ ID NO:26) | Insulin: | FVNQHLCGSHLVEALYLVCGERGFFYTPKT |
| (SEQ ID NO:27) | IGF1: | GPETLCGAELVDALQFVCGDRGFYFNKPTGYG--- |
| (SEQ ID NO:28) | IGF2: | AYRPSETLCGGELVDTLQFVCGDRGFYFSRP--- |

CHIMERIC PEPTIDE ANTAGONIST FOR GPCR135 OR GPCR142

CROSS-REFERENCE TO RELATED APPLICATION

This application claims priority to U.S. Provisional Application No. 60/898,693, filed Jan. 30, 2007.

FIELD OF THE INVENTION

The invention generally relates to a peptidic antagonist that is selective for the G-protein coupled receptors GPRC135 and/or GPCR142 over LGR7.

BACKGROUND OF THE INVENTION

GPCRs are transmembrane receptor proteins that are responsible for the transduction of a diverse array of extra-cellular signals, including hormones, neurotransmitters, peptides, lipids, ions, light, odorants, nucleotides, fatty acid derivatives, and other chemical mediators. See, e.g., WO 2002/00719. GPCRs are of particular importance to drug discovery because they have been established as excellent drug targets: they are the targets of 50% of marketed drugs. An increasing number of diseases have been found to be associated with GPCRs. Drugs targeting GPCRs have been used to treat a wide range of disorders from cardiovascular to gastro-intestinal to CNS and others (Wilson et al., 1998, *British J. of Pharmacology*, 125:1387-1392).

The GPCR-mediated signal transduction event is often initiated upon binding of a specific ligand to the GPCR. Each GPCR is composed of an extracellular N-terminal domain, seven distinct transmembrane segments, and an intracellular C-terminal domain. Binding of the ligand to an extracellular N-terminal domain, transmembrane domain, or intracellular loop of a GPCR results in a conformational change that leads to activation of intracellular heterotrimeric GTP-binding proteins (G proteins) associated with the GPCR. These activated G proteins in turn mediate a variety of intracellular responses that regulate cell physiology. Therefore, the ligand provides means of elucidating the physiological function of the GPCR as well as methods of screening for compounds that regulate the signal transduction activity of the GPCR.

At present, only about two hundred GPCRs are classified as known GPCRs that are activated by around seventy known ligands. Through sequence analyses, it was discovered that GPCRs belong to one of the largest superfamilies of the human genome: evaluated at over one thousand genes encoding GPCRs (Civelli et al., 2001, *Trends in Neurosciences*, 24:230-237). A large number of putative GPCRs are described as orphan receptors because their natural ligands are unknown. Some of these uncharacterized orphan GPCRs may be useful as therapeutic targets. The identification of the specific ligand to a GPCR is the key to harnessing the potential therapeutic benefits of these orphan GPCRs (Howard et al., 2001, *Trends in Pharmacological Sciences*, 22:132-140).

One GPCR of interest is GPCR135, also known as SALPR (Matsumoto et al., 2000, *Gene*, 248:183-189). Relaxin-3 (also known as INSL7) has been found to be a ligand for GPCR135 as well as for GPCR142. See Liu et al., 2003a, *Journal of Biological Chemistry*, 278:50754-50764; Liu et al., 2003b, *Journal of Biological Chemistry*, 278:50765-50770; and International Publication Nos. WO 2004/082598 and WO 2005/014616. Relaxin-3 is a member of the insulin/relaxin superfamily. Members in this family are characterized by two peptide subunits (A-chain and B-chain) linked by three disulfide bonds. Two of the three disulfide bonds are inter-subunit bonds and another one is an intra-chain bond in the B-chain. In the family, insulin, IGF1, and IGF2 have been reported to be involved in the regulation of glucose metabolism and signal through tyrosine kinase/growth factor receptors, which are single transmembrane receptors. Another member of the relaxin/insulin superfamily is Insulin-Like (INSL) 5 (Conklin et al. 1999, *Genomics*, 60(1):50-56), which is believed to be a selective ligand for GPCR142 (see, e.g., U.S. Provisional Application No. 60/580,083, the disclosure of which is incorporated by reference herein). Two other members in the family are relaxin and INSL3, ligands for LGR7 and/or LGR8, which are GPCRs with leucine-rich repeats at the N-terminal extra-cellular domain. See also Hudson et al., 1983, *Nature*, 301:628-631; Hudson et al., 1984, *EMBO J.*, 3:2333-2339.

Relaxin-3, a member of the insulin-relaxin peptide family (Bathgate et al., 2002, *J. Biol. Chem.* 277:1148-1157), and its receptor, GPCR135, are predominantly expressed in the brain (Burazin et al., 2002, *J. Neurochem.* 82:1553-1557). GPCR135 is expressed in many regions of the rodent brain, such as the superior colliculus, sensory cortex, olfactory bulb, amygdala and PVN (see, e.g., Sutton et al., 2004, *Neuroendocrinology* 80:298-307), suggesting potential physiological involvement in neuroendocrine and sensory processing. In vivo studies have further shown that relaxin-3 and GPCR135 are involved in stress response and in the regulation of feeding. Water restraint stress or intracerebroventricular (i.c.v.) CRF infusion induces relaxin-3 expression in cells of the nucleus incertus, where corticotrophin releasing factor receptor 1 is also expressed (Tanaka et al., 2005, *Eur. J. Neurosci.* 21:1659-1670). Central administration of relaxin-3 also induces feeding in rat (McGowan et. al., 2005, *Endocrinology* 146:3295-3300; Hida et al., 2006, *J. Receptor and Signal Transduction* 26:147-158).

In vitro, relaxin-3 activates receptors GPCR135, GPCR142, and LGR7 (Sudo et al., 2003, *J. Biol. Chem.* 278:7855-7862). The predominant brain expression of both relaxin-3 and GPCR135, coupled with their high affinity interaction, reflects that relaxin-3 is the endogenous ligand for GPCR135 (Liu et al., 2003a). In vitro pharmacological characterization, tissue expression profiling, and evolutionary study of GPCR142 and INSL5 indicate that GPCR142 is the endogenous INSL5 receptor (Conklin et al., 1999; Liu et al., 2003b; Chen et al., 2005, *J. Pharmacol. Exp. Ther.* 312: 83-95). The high affinity interaction between relaxin and LGR7 as well as knockout studies demonstrate that relaxin is the endogenous ligand for LGR7 (Zhao et al., 1999, *Endocrinology* 140:445-453; Krajin-Franken et al., 2004, *Mol. Cell Biol.* 24:687-696).

Relaxin-3 activates not only GPCR135 and GPCR142, but also LGR7, which is expressed in both the brain and periphery (Hsu et al., 2000, *Mol. Endocrinol.*, 14:1257-1271; Hsu et al., 2002, *Science*, 295:671-674; Tan et al., 1999, *Br. J. Pharmacol.*, 127:91-98). The chimeric peptide R3/I5, composed of the relaxin-3 B-chain and the INSL5 A-chain, selectively activates GPCR135 over LGR7 (Liu et al., 2005b, *Mol. Pharmacol.*, 67:231-240). See also WO 2006/026344.

Selective agonists having been discovered, there remains a desire to discover selective antagonists of GPCR135 and/or GPCR142 over LGR7. Since GPCR142 is a pseudogene in the rat (Chen et al., 2005) and is not detected in the mouse brain (Sutton et al., 2005, *Neuroendocrinology*, 82:139-150), activation of GPCR142 by central administration of relaxin-3 is not a great concern in murine species. However, potential activation of LGR7 by relaxin-3 remains problematic. LGR7 is expressed in the brain and is reported to play an important role in drinking (Thornton et al., 1995, *J. Neuroendocrinol.*, 3:165-169; McGowan et. al., 2005) and potentially other physiological functions (Wilson et al., 2006, *Neurosc.i Lett.*, 393:160-164; Nistri et al., 2005, *Curr. Neurovasc. Res.*, 2:225-233; Sherwood, 2004, *Endocr Rev.*, 25:205-234).

SUMMARY OF THE INVENTION

Chimeric polypeptides that are selective antagonists of GPCR135 and/or GPCR142 over LGR7 have now been found, comprising: a B-chain having the amino acid sequence RAAPYGVRLCGREFIRAVIFTCR (SEQ ID NO:15); and an A-chain having the amino acid sequence <EDLQTL-CCTDGCSMTDLSALC (SEQ ID NO:19) (where "<E" represents pyro-Glu) or DVLAGLSSSCCKWGCSKSEISSLC (SEQ ID NO:13). In a preferred embodiment, the amino acid sequence of the A-chain is <EDLQTLCCTDGCSMTDL-SALC (SEQ ID NO:19).

Exemplary characteristics and advantages of the invention will become apparent from the detailed description below taken in conjunction with the appended drawing figures.

BRIEF DESCRIPTION OF THE DRAWINGS

FIG. 7 provides an amino acid sequence comparison of the B-chains from peptides in the insulin/relaxin family. Amino acid residues corresponding to $Gly^{11}$ and $Gly^{23}$ of the relaxin-3 B-chain are shown in bold letter.

DETAILED DESCRIPTION OF INVENTION AND ITS PREFERRED EMBODIMENTS

Figure 1:
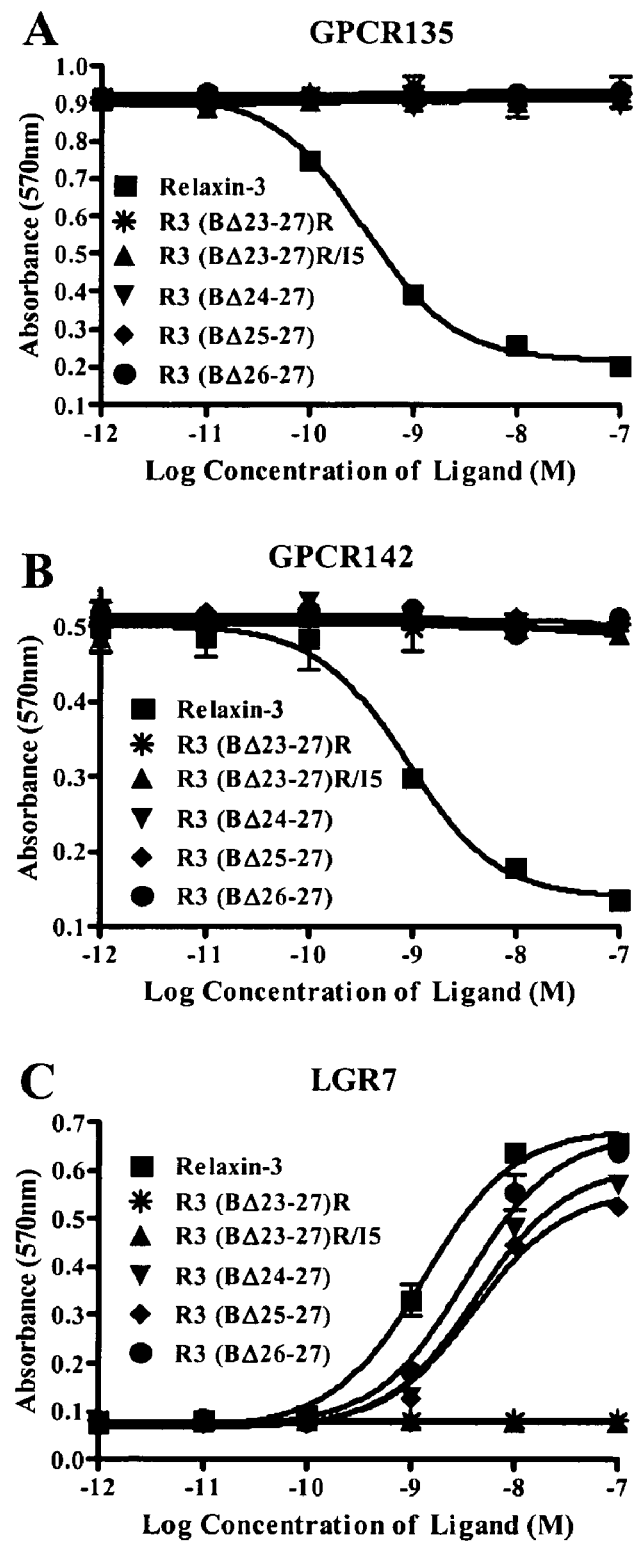
FIG. 1 provides a characterization of mutant relaxin-3 peptides as ligands for human GPCR135, GPCR142, and LGR7. The truncated peptides were tested for their GPCR135 and GPCR142 agonist activity using SK-N-MC/CRE-β-gal cells expressing either human GPCR135 (A) or GPCR142 (B). Agonists for GPCR135 or GPCR142 inhibit forskolin induced β-galactosidase (β-gal) expression. The LGR7 agonist activity of the truncated peptides was tested using SK-N-MC/CRE-β-gal cells expressing $G_{\alpha s}$-linked human LGR7 (C). Human relaxin-3 was used as positive control in both cases. β-gal expression was measured by colorimetric assay using CPRG as the substrate and reading the absorbance at 570 nm. The $EC_{50}$ values are the mean±SEM (listed in Table 3 below).

For the sake of brevity, the disclosures of all publications cited in this specification are incorporated by reference herein. Unless defined herein or otherwise indicated below, all technical and scientific terms used herein have the same meaning as commonly understood in the art.

As used herein, the terms "comprising", "including", and "containing" are used in their open, non-limiting sense.

A chimeric polypeptide referred to as R3(BΔ23-27)R/I5 has now been developed, which comprises the relaxin-3 B-chain with a truncation at the C-terminus ($Gly^{23}$-$Trp^{27}$, the GPCR135 activation domain) plus an Arg residue and the A-chain from INSL5. This high-affinity GPCR135 antagonist does not interact with LGR7.

In the process of designing R3(BΔ23-27)R/I5, relaxin-3 mutants R3(BΔ23-27)R, R3(BΔ24-27), R3(BΔ25-27), and R3(BΔ26-27) were initially prepared. Pharmacological characterization shows that these peptides are GPCR135 antagonists, with R3(BΔ23-27)R being the most potent. R3(BΔ24-27), R3(BΔ25-27) and R3(BΔ26-27) were found, however, to also be potent LGR7 agonists. On the other hand, R3(BΔ23-27)R was found to be a low-affinity LGR7 ligand ($IC_{50}$~200 nM). To further increase selectivity, the A-chain of relaxin-3 was replaced with the A-chain of INSL5, a strategy used in the past to create specific GPCR135/GPCR142 agonist R3/I5 (Liu et al., 2005b). The resulting peptide, R3(BΔ23-27)R/I5, proved to be a selective high-affinity GPCR135 antagonist having essentially no affinity to LGR7. R3(BΔ23-27)R/I5 was also shown to displace GPCR135 binding sites in native tissue (rat brain tissue sections, FIG. 5).

As apparent from the Examples below, administration of GPCR135-specific antagonist R3(BΔ23-27)R/I5 blocks increased feeding in satiated Wistar rats following i.c.v. dosing of R3/I5 (a selective GPCR135 agonist). Thus, a therapeutically effective amount of the chimeric polypeptide R3(BΔ23-27)R/I5 may be used pharmaceutically to suppress appetite or to treat obesity. The polypeptide may also be used in drug research and development, for example, as a reference compound or comparator in an assay for screening small molecules to identify antagonists of GPCR135 that may be administered to suppress appetite or treat obesity.

designated as R3(BΔ23-27)/I5. All mutant relaxin-3 peptide coding regions were created by a two-step PCR process using primers shown in Table 1.

TABLE 1

Primers used to construct truncated relaxin-3 peptide coding regions

| Mutants | 5' end | | 3' end | | Full length | |
|---|---|---|---|---|---|---|
| | 5' primer | 3' primer | 5' primer | 3' primer | 5' primer | 3' primer |
| R3(BΔ23-27) | P1 | P3 | P4 | P2 | P1 | P2 |
| R3(BΔ24-27) | P1 | P4 | P6 | P2 | P1 | P2 |
| R3(BΔ25-27) | P1 | P7 | P8 | P2 | P1 | P2 |
| R3(BΔ26-27) | P1 | P9 | P10 | P2 | P1 | P2 |
| R3(BΔ23-27)/I5 | P1 | P3 | P4 | Pi5 | P1 | Pi5 |

Primer Sequences

P1: 5'-ATGCTACTGCAGGCCGCCATGCTGACCGCAGCGTTG-3'
    (SEQ ID NO: 1)

P2: 5'-ATGATAGGATCCCTAGCAAAGGCTACTGATTTCACTTTTGCTACAC-3'
    (SEQ ID NO: 2)

P3: 5'-GATGTCTGATCGTCTTCGTCTGCAGGTGAAGATGACTGCTCGGAT-3'
    (SEQ ID NO: 3)

P4: 5'-GTCATCTTCACCTGCAGACGAAGACGATCAGACATCCTGGCCCAC-3'
    (SEQ ID NO: 4)

P5: 5'-GATGTCTGATCGTCTCCGCCGCCCGCAGGTGAAGATGACTGCTCG-3'
    (SEQ ID NO: 5)

P6: 5'-TCATCTTCACCTGCGGGCGGCGGAGACGATCAGACATCCTGGCCC-3'
    (SEQ ID NO: 6)

P7: 5'-GATGTCTGATCGTCTCCGCCGGCCCCCGCAGGTGAAGATGACTGC-3'
    (SEQ ID NO: 7)

P8: 5'-TTCACCTGCGGGGGCCGGCGGAGACGATCAGACATCCTGGCCCAC-3'
    (SEQ ID NO: 8)

P9: 5'-GTCTGATCGTCTCCGCCGGGAGCCCCCGCAGGTGAAGATGAC-3'
    (SEQ ID NO: 9)

P10: 5'-CCTGCGGGGGCTCCCGGCGGAGACGATCAGACATCCTGGCCC-3'
     (SEQ ID NO: 10)

Pi5: 5'-ACTAGAGGATCCTTAGCAAAGAGCACTCAAATCAGTCATG-3'
     (SEQ ID NO: 11)

EXAMPLES

Materials and Methods

Generation of Relaxin-3 and R3/I5 Peptides with B-Chain C-Terminal Truncations:

All peptides were generated recombinantly in mammalian cells in a manner similar to the production of relaxin-3 as described by Liu et al., 2003a. Relaxin-3 peptides with residues $Gly^{23}$-$Trp^{27}$, $Gly^{24}$-$Trp^{27}$, $Ser^{25}$-$Trp^{27}$, or $Arg^{26}$-$Trp^{27}$ deleted from the B-chain are designated herein as R3(BΔ23-27), R3(BΔ24-27), R3(BΔ25-27), R3(BΔ26-27), respectively. A chimeric relaxin-3 peptide with a truncated relaxin-3 B-chain ($Gly^{23}$-$Trp^{27}$ deleted) and the A-chain from INSL5 is In the first round PCR, overlapping 5' end and 3' end coding regions for the truncated peptides were PCR amplified. The human relaxin-3-RR cDNA construct (Liu et al., 2003a) was then used as the template in the first step PCR reactions for R3(BΔ23-27), R3(BΔ24-27), R3(BΔ25-27) and R3(BΔ26-27). For R3(BΔ23-27)/I5, the R3/I5 expression construct (Liu et al., 2005b) was used as the template for PCR reactions. The first step PCR products (5' end and 3' end) were mixed and served as the templates for the second round PCR reactions using primers P1 and P2 (i.e., Pi5 for R3(BΔ23-27)/I5) as listed in Table 1. All PCR reactions were run under conditions of 94° C., 20 seconds; 65° C., 20 seconds; and then 72° C., 1 minute, for 20 cycles. The final PCR products were cloned into a modified pCMV-SPORT1 vector that contains a signal peptide for secretion coding region, which is followed by a FLAG peptide coding region for affinity purification (Liu et al., 2003a). All cDNAs for mutant relaxin-3 peptides were sequence verified.

The truncated peptides (except R3(BΔ23-27)/I5) have the intact A-chain of the wild type relaxin-3 but have different C-terminal truncations of the B-chains. R3(BΔ23-27)/I5 contains the A-chain of human INSL5 with a truncated relaxin-3 B-chain. The amino acid sequences for relaxin-3 and the mutant peptides are shown in Table 2.

cAMP concentration in these cells is associated with increased β-gal expression, which can be measured using Chlorophenol Red-β-D-Galactopyranoside (CRGP) as a substrate and reading the optical absorbance at 570 nm.

TABLE 2

| Peptide | B-Chain | A-Chain |
| --- | --- | --- |
| Relaxin-3 | RAAPYGVRLCGREFIRAVIFTCGGSRW (SEQ ID NO: 12) | SVLAGLSSSCCKWGCSKSEISSLC (SEQ ID NO: 13) |
| R3 (BΔ23-27) | RAAPYGVRLCGREFIRAVIFTC (SEQ ID NO: 14) | DVLAGLSSSCCKWGCSKSEISSLC (SEQ ID NO: 13) |
| R3 (BΔ23-27)R | RAAPYGVRLCFREFIRAVIFTC<u>R</u> (SEQ ID NO: 15) | DVLAGLSSSCCKWGCSKSEISSLC (SEQ ID NO: 13) |
| R3 (BΔ24-27) | RAAPYGVRLCGREFIRAVIFTCG (SEQ ID NO: 16) | DVLAGLSSSCCKWGCSKSEISSLC (SEQ ID NO: 13) |
| R3 (BΔ25-27) | RAAPYGVRLCGREFIRAVIFTCGG (SEQ ID NO: 17) | DVLAGLSSSCCKWGCSKSEISSLC (SEQ ID NO: 13) |
| R3 (BΔ26-27) | RAAPYGVRLCGREFIRAVIFTCGGS (SEQ ID NO: 18) | DVLAGLSSSCCKWGCSKSEISSLC (SEQ ID NO: 13) |
| R3/I5 | RAAPYGVRLSCGREFIRAVIFTCGGSRW (SEQ ID NO: 12) | <EDLQTLCCTDGCSMTDLSALC (SEQ ID NO: 19) |
| R3 (BΔ23-27)/I5 | RAAPYGVRLCGREFIRAVIFTC (SEQ ID NO: 14) | <EDLQTLCCTDGCSMTDLSALC (SEQ ID NO: 19) |
| R3 (BΔ23-27)R/I5 | RAAPYGVRLCGREFIRAVIFTC<u>R</u> (SEQ ID NO: 15) | <EDLQTLCCTDGCSMTDLSALC (SEQ ID NO: 19) |

All recombinant peptides were co-expressed with the furin protease in COS-7 cells for efficient removal of the C-chain (Liu et al, 2003a). The N-terminally FLAG-tagged peptides were first purified using an anti-FLAG affinity column and then the tag was removed with enterokinase (Novagen). The peptides, free of the FLAG tag, were then further purified by reversed phase HPLC. The purified peptides were analyzed by mass spectrometry as described (Liu et al., 2003a) to verify the peptide identities. R3(B23-27)R and R3(BΔ23-27)R/I5, which are derivatives of R3(B23-27) and R3(BΔ23-27)/I5 respectively, have an extra Arg residue at the C-terminus of the B-chain due to incomplete processing (Table 2).

Radioligand Binding Assays:

COS-7 cells in 24-well tissue culture plates transiently expressing GPCR135, GPCR142 or LGR7 were used in radioligand binding assays as described by Liu et al., 2005a, *J. Biol. Chem.*, 280:292-300. $^{125}$I-Relaxin-3/INSL5 ($^{125}$I-R3/I5), a radiolabeled chimeric peptide with the human relaxin-3 B-chain and the human INSL5 A-chain (Liu et al., 2005b), was used at a final concentration of 50 pM as the tracer to characterize the binding properties of all truncated relaxin-3 peptides for GPCR135 and GPCR142. $^{125}$I-relaxin-2 (PerkinElmer Biosciences, Boston) was used at a final concentration of 50 pM to characterize the binding properties of the truncated peptides for the relaxin receptor (LGR7). The results were analyzed by GraphPad Prism 4.0 software (Graphpad, San Diego). The $IC_{50}$ values, which are the ligand concentrations that inhibited 50% of the maximum specific binding, were then calculated.

Agonist and Antagonist Analysis for Truncated Peptides:

All peptides were tested for their GPCR135, GPCR142, and LGR7 agonist activities in SK-N-MC/CRE cells expressing the relevant receptors as described by Liu et al., 2005b. SK-N-MC/CRE-β-gal cells harbor a β-galactosidase (β-gal) gene under the control of a CRE promoter. An increase in GPCR135 and GPCR142 are coupled with $G\alpha_i$ proteins, therefore agonists inhibit foskolin-stimulated β-gal expression in GPCR135 or GPCR142 expressing cells. LGR7 is Gs-linked, therefore agonists stimulate β-gal expression in LGR7 expressing cells. R3(BΔ23-27)R/I5 was tested for its ability to produce a rightward-shift in relaxin-3's dose-response curve in the presence of 10 nM, 100 nM, or 1 μM R3(BΔ23-27)R/I5 to demonstrate functional antagonism. Wild type relaxin-3 peptide was used as positive control in all experiments. The results were analyzed using GraphPad Prism 4.0 software. The $EC_{50}$ values, which are the ligand concentrations that stimulate 50% of the maximum responses, were then calculated. The agonism and antagonism of each peptide for rat GPCR135 were tested in the same way as the human GPCR135 using SK-N-MC/CRE-β-gal cells stably expressing rat GPCR135. The agonism and antagonism of peptides for rat LGR7 was assayed using a cAMP luminescence assay. Briefly, HEK293 cells were transiently transfected with a cDNA construct expressing rat LGR7 (Sutton et al., 2004). Two days post transfection, cells were detached with PBS+10 mM EDTA and plated at a density of 25,000 cells/well in 96-well white opaque plates (Thermo Electron Corporation, Cat #7571). To test the agonism of R3(BΔ23-27)R/I5, cells expressing rat LGR7 were stimulated with different concentrations of R3(BΔ23-27)R/I5 with relaxin-3 as the positive control. To test the antagonism of R3(BΔ23-27)R/I5 for rat LGR7, different concentrations of relaxin-3 were added to cells expressing rat LGR7 in the presence of 10 nM, 100 nM, or 1 μM of R3(Δ23-27)R/I5. Cells were then incubated at room temperature for 1 hr. The cAMP in the cells was measured with a cAMP detection kit (DiscoveRx HitHunter, Cat. #90-0041) according to the manufacturer's protocol. The results were analyzed using GraphPad Prism 4.0 software.

Autoradiographic Studies:

R3(BΔ23-27)R/I5 peptide was evaluated pharmacologically using endogenous GPCR135 from rat brain slices in autoradiographic studies as described by Sutton et al., 2004. Briefly, $^{125}$I-R3/I5 was applied in a binding buffer to rat brain slices. Unlabeled human relaxin-3 or R3(BΔ23-27)R/I5 was used at various concentrations as competitors to displace GPCR135 binding of $^{125}$I-R3/I5.

Animal Studies:

Experimentally naïve, male Wistar rats (Charles River, Wilmington, Mass.) weighing 200-225 grams at the time of arrival were used. The animals were initially housed at two per cage and given a one-week acclimation period to the vivarium prior to i.c.v. cannula implantation. All animals had free access to food and water throughout the experiment and were not food deprived prior to behavioral testing. The animal colony was maintained at 22±2° C. during a 12-hr light/12-hr dark illumination cycle with lights on from 0600 to 1800 hours. All behavioral testing occurred during the light phase between 0800 and 1600 hrs. All studies were carried out in accordance with the Guide for the Care and Use of Laboratory Animals as adopted and promulgated by the US National Institutes of Health.

Following the acclimation period, the animals (n=23) were anesthetized with 4% isoflurane and surgically implanted with a 20-gauge guide cannula aimed at the lateral ventricle. Guide cannulae (Plastics One, Roanoke, Va.) were unilaterally implanted using a stereotaxic apparatus (David Kopf, Tujunga, Calif.) using the following coordinates relative to Bregma (flat skull): AP=+1.0 mm, ML=−1.3 mm, DV=−3.8 mm from the top of the skull (Paxinos and Watson, 1998, *The Rat Brain in Stereotaxin Coordinates* (4th ed.), Academic Press, San Diego, USA). Three screws were mounted in the skull and covered with dental cement, which served as an anchor for the guide cannula. Following surgery, an injection of buprenorphine (0.1 mg/kg S.C.) was administered prophylactically for pain. Animals were then individually housed and given a 7-day recovery period from surgery. During the surgical recovery period, the animals were handled 2-3 times to minimize stress effects that might occur due to handling at the time of behavioral testing.

The testing apparatus consisted of a plastic cage (containing no bedding) normally used to house rats and a wire grid was placed on the floor of the cage. A food hopper and drinking spout were located on opposite walls of the cage. The drinking spout was connected to an automated watering system and thereby delivered water to the animal throughout the session(s) on demand.

A predetermined amount of standard rat chow (Formulab Diet No. 5008, which contained 23.0% protein and 6.5% fat) was placed in the food hopper at the start of the 4 hr session(s). The amount of food remaining in the food hopper was determined by subtracting the weight of the food at 1 and 4 hrs from the initial food weight (i.e., weight of the food at the start of the session). Food crumbs detected on the floor of the apparatus were included in the determination of food weights.

The peptides (i.e, R3/I5, R3(BΔ23-27)R/I5) were dissolved in vehicle (sterile physiological saline plus 0.1% bovine serum albumin). All solutions were infused in a 5 μl volume.

Following the surgical recovery period, the animals were randomly assigned to one of the four treatment conditions (i.e., vehicle (5 μl)+vehicle (5 μl); vehicle (5 μl)+R3/I5 (10 μg); R3(BΔ23-27)R/I5 (10 μg)+vehicle (5 μl); R3(BΔ23-27)R/I5 (10 μg)+R3/I5 (10 μg)).

Testing consisted of a two-day protocol. Day 1 served as the baseline session. No injections were administered during this session and it served as a habituation period to the testing apparatus, while also providing a baseline measure of food intake. Day 2 served as the test session. Immediately prior to this session, all animals were removed from their home cage and two infusions were administered directly into the lateral ventricle. Test substances were given via a pre-loaded catheter without removing the catheter between injections. A 0.5-μl air bubble separated each injection to prevent mixing. The animals were first infused with vehicle (5 μl) or R3(BΔ23-27)R/I5 (10 μg), followed by a second infusion that consisted of vehicle (5 μl) or R3/I5 (10 μg). The infusions were separated by 10 minutes and the injection needle remained in the guide cannula for one minute following the termination of the final infusion. Following the second infusion, the animals were placed in the testing apparatus and food intake was measured at 1 and 4 hrs during a 4 hr session. Food intake measured at the end of the session served as a measure of total food intake. All animals were euthanized with carbon dioxide and cannula placements were verified at the end of behavioral testing.

Results

Expression and Purification of Mutant Relaxin-3 Peptides with a Truncation at the C-Terminus of the B-Chain:

Expression constructs encoding mutant relaxin-3 peptides with truncations at the C-terminus of the B-chain were created similarly to recombinant expression of wild type relaxin-3 as previously described (Liu et al., 2003a). The C-termini of various mutant relaxin-3 B-chains were modified so that amino acids Gly$^{23}$-Trp$^{27}$ (R3(BΔ23-27)), Gly$^{24}$-Trp$^{27}$ (R3(BΔ24-27)), Ser$^{25}$-Trp$^{27}$ (R3(BΔ25-27)), or Arg$^{26}$-Trp$^{27}$ (R3(BΔ26-27)) were deleted in the mature peptide. The junctions between the B-chain, C-chain, and A-chain contain a furin cleavage site (Arg-Arg-Arg-Arg) for efficient cellular processing when co-transfected with furin (Liu et al., 2003a). Upon cellular processing to the mature peptide, the arginines were removed by furin and endogenous carboxypeptidase-B (Hosaka et al., 1991, *J. Biol. Chem.*, 266:12127-12130), yielding the mature peptide sequences shown in Table 2. The recombinant peptides secreted into the cell culture medium were affinity purified with an anti-FLAG affinity column. The peptides were then cleaved with enterokinase to yield the untagged peptides, which were further purified by HPLC. Mass spectrometry analysis showed that R3(BΔ24-27), R3(BΔ25-27) and R3(BΔ26-27) had molecular masses of 5013 Da, 5070 Da and 5157 Da, respectively, which matched the predicted molecular masses. However, the R3(BΔ23-27) product had a molecular mass of 5112 Da, which was 156 Da greater than the predicted molecular mass (4956 Da). The 156 Da difference is consistent with a residual C-terminal Arg. This residual C-terminal Arg on the B-chain was probably the result of steric hinderance that prevented carboxypeptidase-B from cleaving the last Arg residue. This peptide was designated R3(BΔ23-27)R to reflect the additional Arg at the C-terminus of the B-chain. Peptide R3(BΔ23-27)/I5 was designed to contain a truncated relaxin-3 B-chain (Gly23-Trp27 removed) and the A-chain from INSL5. However, mass analysis of the resulted peptide indicated that it had a mass of 4851 Da, again 156 Da greater than the predicted mass of R3(BΔ23-27)/I5 (4695 Da), indicating it also had an additional Arg residue at the C-terminus of its B-chain. This peptide was therefore designated R3(BΔ23-27)R/I5.

In Vitro Characterization of Truncated Relaxin-3 Peptides as Ligands for GPCR135, GPCR142 and LGR7:

Mutant relaxin-3 peptides R3(BΔ23-27)R, R3(BΔ24-27), R3(BΔ25-27), R3(BΔ26-27), and R3(BΔ23-27)R/I5 were tested in GPCR135, GPCR142, and LGR7 radioligand binding assays. The results are summarized in Table 3.

TABLE 3

IC$_{50}$ and EC$_{50}$ values of relaxin-3 and mutant peptides for human GPCR135, GPCR142, and LGR7

| Peptides | IC$_{50}$ (nM)[a] | | | EC$_{50}$ (nM)[b] | | |
|---|---|---|---|---|---|---|
| | GPCR135 | GPCR142 | LGR7 | GPCR135 | GPCR142 | LGR7 |
| Relaxin-3 | 0.53 ± 0.09 | 1.49 ± 0.12 | 2.41 ± 0.23 | 0.35 ± 0.06 | 0.95 ± 0.14 | 1.3 ± 0.15 |
| R3(BΔ23-27)R | 0.95 ± 0.14 | 3.91 ± 0.56 | ~200 | NA | NA | NA |
| R3(BΔ23-27)R/I5 | 0.67 ± 0.11 | 2.29 ± 0.23 | NA | NA | NA | NA |
| R3(BΔ24-27) | 13.5 ± 1.84 | 18.9 ± 2.31 | 8.9 ± 1.21 | NA | NA | 4.3 ± 0.57 |
| R3(BΔ25-27) | 9.5 ± 1.64 | 11.9 ± 1.34 | 7.9 ± 0.72 | NA | NA | 4.1 ± 0.61 |
| R3(BΔ26-27) | 11.5 ± 1.96 | 9.5 ± 1.28 | 6.3 ± 0.45 | NA | NA | 3.3 ± 0.42 |

Notes.
[a]IC$_{50}$ values (mean ± SEM) = the concentrations of ligands that displaced 50% of the specific binding in the competition binding assay.
[b]EC$_{50}$ values (mean ± SEM) = the concentrations of ligands that stimulated agonistic responses by 50%.
c: NA = no affinity was observed in radioligand binding assay or no agonist activity was observed in the functional assay.

Figure 2:
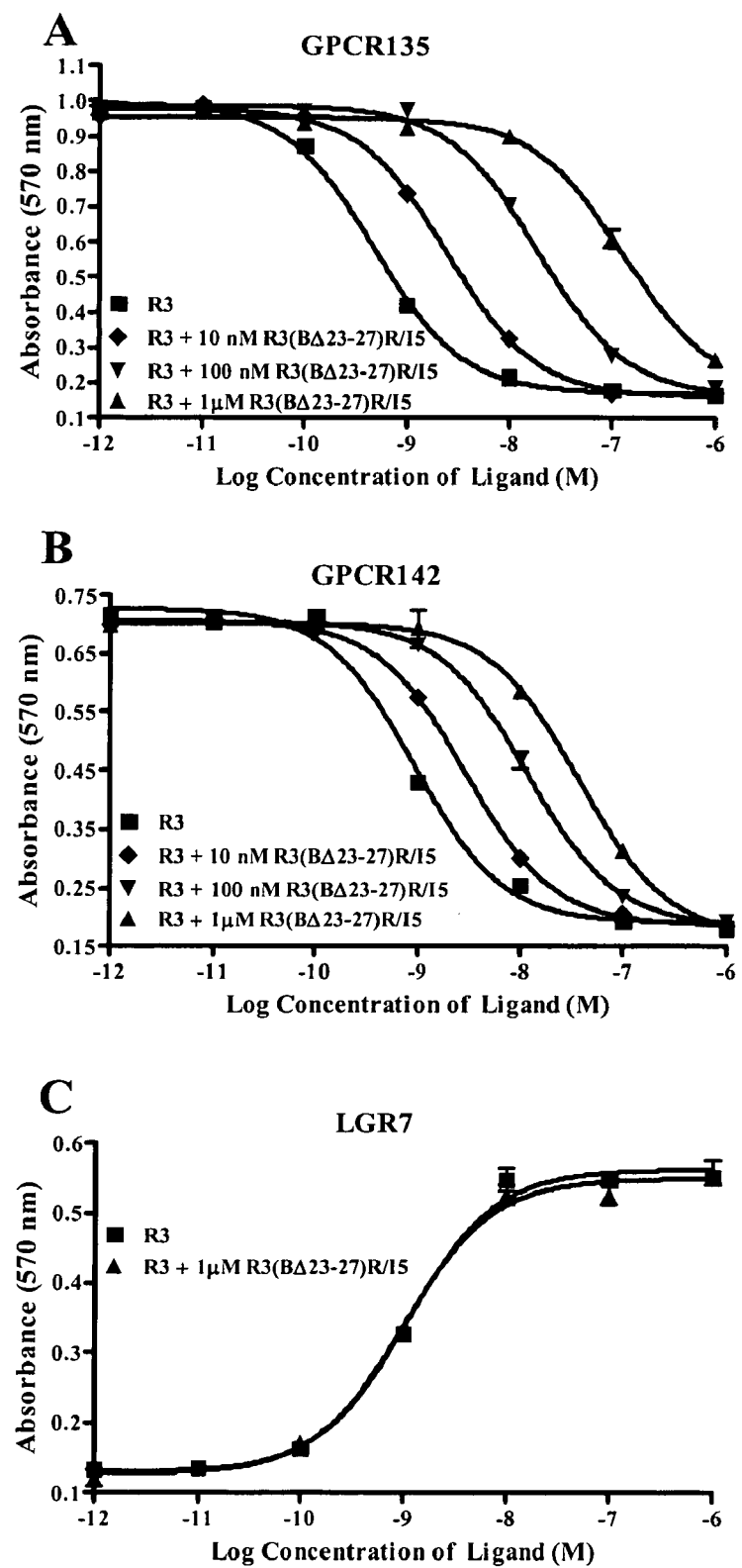
FIG. 2 shows a characterization of R3(BΔ23-27)R/I5 as an antagonist for human GPCR135 and GPCR142. In a functional assay using SK-N-MC/CRE-β-gal cells expressing human GPCR135 (A), GPCR142 (B) or LGR7 (C), ascending concentrations of relaxin-3 (R3) were used to generate dose response curves either in the absence or presence of 10 nM, 100 nM or 1 µM R3(BΔ23-27)R/I5. For $G_{\alpha i}$ linked GPCR135 and GPCR142, the assay was performed as inhibition of forskolin-induced β-gal expression. LGR7 is linked to $G_{\alpha s}$, therefore addition of forskolin is not necessary. The antagonism of R3(BΔ23-27)R/I5 is indicated by the rightward-shift of the relaxin-3's dose-response curve. R3(BΔ23-27)R/I5 does not affect relaxin-3's stimulation of LGR7. β-gal expression was measured by colorimetric assay using CPRG as the substrate and reading the absorbance at 570 nm.
Figure 3:
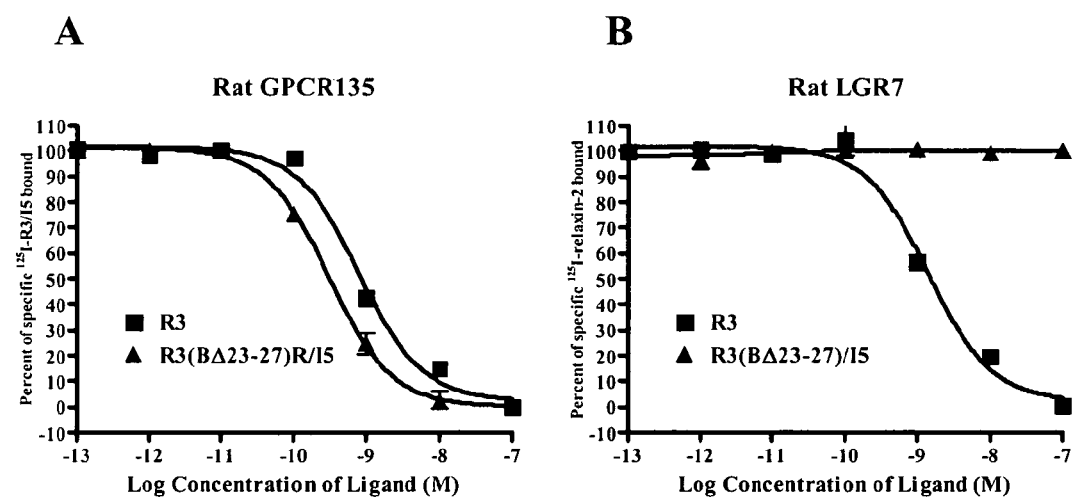
FIG. 3 illustrates that R3(BΔ23-27)R/I5 is bound by recombinant rat GPCR135 with high affinity, but not by rat LGR7. COS-7 cells transiently expressing recombinant rat GPCR135 or LGR7 were used to characterize the binding affinity of rat GPCR135 (A) and LGR7 for (B) R3(BΔ23-27) R/I5. $^{125}$I-R3/I5 was used as the tracer for GPCR135 and $^{125}$I-relaxin-2 was used as the tracer for LGR7 binding. Various concentrations of R3(BΔ23-27)R/I5 were used as the competitor and unlabeled human relaxin-3 was used as the positive control in the binding assay.
Figure 4:
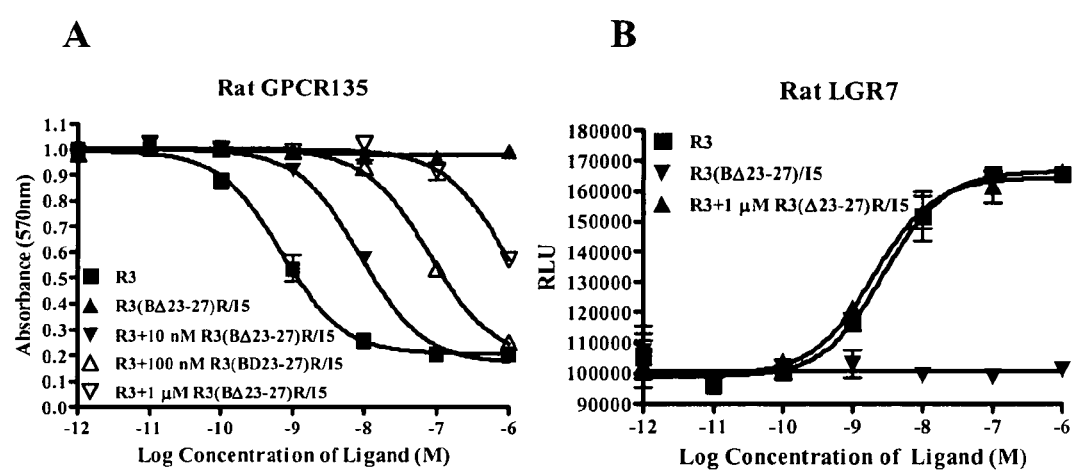
FIG. 4 illustrates that R3(BΔ23-27)R/I5 does not activate GPCR135 but dose-dependently rightward-shifts relaxin-3's dose response curve for recombinant rat GPCR135 (A). The figure also shows that R3(BΔ23-27)R/I5 (1 µM) does not affect relaxin-3's function on rat LGR7 (B). Human relaxin-3 was used as positive control to stimulate GPCR135 or LGR7. SK-N-MC/CRE-β-gal cells stably expressing rat GPCR135 (A) and HEK293 cell transiently expressing rat LGR7 (B) were used in the functional characterization of R3(BΔ23-27) R/I5. Recombinant rat GPCR135 agonist activity was measured as inhibition of forskolin-induced β-gal expression, while recombinant rat LGR7 agonist activity was measured using a cAMP luminescent assay kit to detect the ligand-stimulated changes in cAMP.
Figure 5:
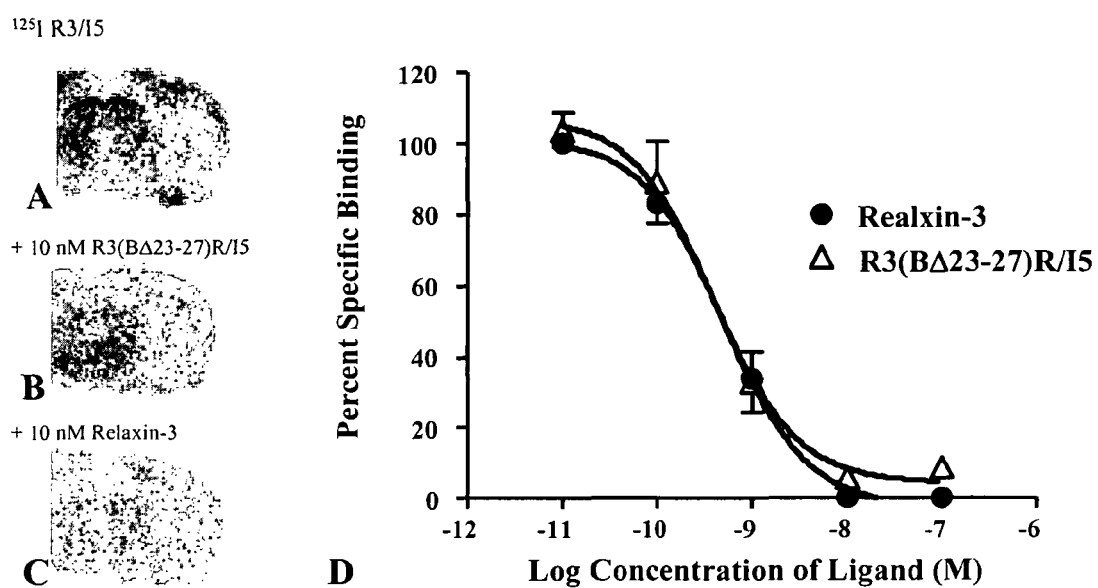
FIG. 5 provides autoradiograms of $^{125}$I-R3/I5 binding sites in the rat brain (A) with competition by relaxin-3 (10 nM, B) or R3(BΔ23-27)R/I5 (10 nM, C), and a dose-response curve for R3(BΔ23-27)R/I5 as the competitor in the binding assay on rat brain slices (D). A dose-response curve for human relaxin-3 is included for comparison (D). Nonspecific binding was determined using 1 µM unlabeled relaxin-3.

The results tabulated above show that human GPCR135 and GPCR142 have high affinities for R3(BΔ23-27)R but human LGR7 has a low affinity for this peptide. Human GPCR135 and GPCR142 have high affinities for R3(BΔ23-27)R/I5, but human LGR7 shows no affinity for the peptide (Table 3). GPCR135 and GPCR142 have moderately high affinities for R3(BΔ24-27), R3(BΔ25-27) and R3(BΔ26-27), while human LGR7 binds these peptides with high affinity (Table 3). Truncated relaxin-3 peptides were tested on SK-N-MC/CRE-β-gal cells stably expressing GPCR135, GPCR142 or LGR7 receptors. Since GPCR135 and GPCR142 are coupled to G$_{\alpha i}$ proteins (Liu et al 2003a, b), the agonist activities of the mutant peptides were tested as inhibition of forskolin-induced β-gal expression in SK-N-MC/CRE-β-gal cells expressing GPCR135 or GPCR142 (Liu et al., 2005b). None of the truncated relaxin-3 peptides demonstrate significant agonist activity for human GPCR135 (FIG. 1A) or GPCR142 (FIG. 1B). LGR7 is linked to G$_{\alpha s}$ proteins (Hsu et al., 2002), therefore, LGR7 agonism of the truncated relaxin-3 peptides was compared by testing for stimulation of β-gal expression in SK-N-MC/CRE-β-gal cells expressing LGR7 (Liu et al., 2005b). In contrast to GPCR135 and GPCR142, the results showed that R3(BΔ24-27), R3(BΔ25-27), and R3(BΔ26-27) are high potency human LGR7 agonists with EC$_{50}$ values from 3 to 5 nM (FIG. 1C, Table 3). R3(BΔ23-27)R and R3(BΔ23-27)R/I5 showed no LGR7 agonist activity (FIG. 1C). Human GPCR135 and GPCR142 bind R3(BΔ23-27)R/I5 with high affinities but neither receptor shows agonist activity. LGR7 has little or no affinity for R3(BΔ23-27)R/I5, suggesting that R3(BΔ23-27)R/I5 is a selective antagonist for human GPCR135 over LGR7. The antagonism of human GPCR135, GPCR142 and LGR7 by R3(BΔ23-27)R/I5 was compared using the functional reporter assay and the results show that R3(BΔ23-27)R/I5 dose-dependently shifted relaxin-3's agonism curves for GPCR135 (pA2=9.1, FIG. 2A) and GPCR142 (pA2=8.2, FIG. 2B) to the right. In contrast, R3(BΔ23-27)R/I5 does not affect relaxin-3's agonism for LGR7 (FIG. 2C) at doses of up to 1 μM. The pharmacology of R3(BΔ23-27)R/I5 was also studied using recombinant rat GPCR135 and LGR7. Recombinant rat GPCR135 binds R3(BΔ23-27)R/I5 with high affinity (IC$_{50}$=0.25 nM, FIG. 3A) but rat LGR7 lacks affinity for this peptide (FIG. 3B). In a functional reporter assay, R3(BΔ23-27)R/I5 potently shifted relaxin-3's agonism curve for recombinant rat GPCR135 (pA2=9.6, FIG. 4A) to the right, but did not affect relaxin-3's agonism for recombinant rat LGR7 (FIG. 4B). R3(BΔ23-27)R/I5 was further characterized using endogenous GPCR135 in rat brain slices (FIG. 5). Full displacement of $^{125}$I-R3/I5 binding sites in rat brain sections by relaxin-3 and R3(BΔ23-27)R/I5 was observed at 10 nM. The IC$_{50}$ values for rat brain binding of relaxin-3 and R3(BΔ23-27)R/I5 were 0.5±0.1 nM and 0.4±0.1 nM, respectively.

R3(BΔ23-27)R/I5 Inhibits R3/I5 Stimulated Food Intake in Satiated Rats:

R3/I5 and R3(BΔ23-27)R/I5 were tested in vivo for their abilities to modulate feeding behaviors in rats. When 10 μg of R3/I5 was administrated i.c.v. to satiated Wistar rats, food intake was stimulated (n=6) for both the first hour (FIG. 6A) and over 4 hours (FIG. 6B) after R3/I5 administration. Intracerebroventricular administration of 10 μg R3(BΔ23-27)R/I5 prior to the R3/I5 dose blocked R3/I5 stimulated food intake. To assure that the effect on food intake could not be attributed to pre-existing group differences in consumption rates, a baseline measure of food intake (i.e., Day 1) was collected prior to introducing any of the treatments. Untreated-satiated animals assigned to the different treatment conditions exhibited similar levels of food intake at 1 hr and 4 hrs on the baseline day (data not shown). An ANOVA (Treatment×Day) was used to determine the effect of treatment on food consumption for the four treatment conditions shown (FIGS. 6A and 6B). The amount of food consumed at 1 hr and the total amount of food consumed during the 4 hr test session after dosing (i.e., Day 2) were used in the analyses. There was a significant effect of Treatment at 1 hr [F(3,19)=6.103, p=0.0044] and 4 hrs [F(3,19)=8.859, p=0.0007]. A Newman-Keuls' test revealed that animals infused with vehicle+R3/I5 consumed significantly more food at 1 hr than animals assigned to the other treatment conditions (cf. vehicle+vehicle (\*\*p<0.01), R3(BΔ23-27)R/I5+vehicle (#p<0.05), and R3(BΔ23-27)R/I5+R3/I5 (\*\*p<0.01). In addition, the increased food intake exhibited by animals infused with vehicle+R3/I5 was completely blocked when animals were pretreated with R3(BΔ23-27)R/I5 10 min prior to the R3/I5 injection (\*\*p<0.01 cf. vehicle+R3/I5); intake amounts for R3(BΔ23-27)R/I5+R3/I5 infused animals were not significantly different from vehicle+vehicle infused animals (p>0.05).

A separate post hoc analysis (i.e., Newman-Keuls' test) performed on food intake measured at 4 hrs revealed that animals infused with vehicle+R3/I5 consumed significantly more food during an entire session than animals infused with vehicle+vehicle (\*\*\*p<0.001), R3(ΔB23-27)R/I5+vehicle (#p<0.05), or R3(ΔB23-27)R/I5+R3/I5 ($p<0.1). Similar to the effect observed at 1 hr, R3(BΔ23-27)R/I5+R3/I5 infused animals showed a significant reduction in their total food consumption compared to animals given R3/I5 (i.e., 4 hr intake). The total amount of food consumed by R3(BΔ23-27)R/I5+R3/I5 infused animals during an entire session was not significantly different from vehicle+vehicle infused animals (p>0.05).

Discussion

Figure 6:
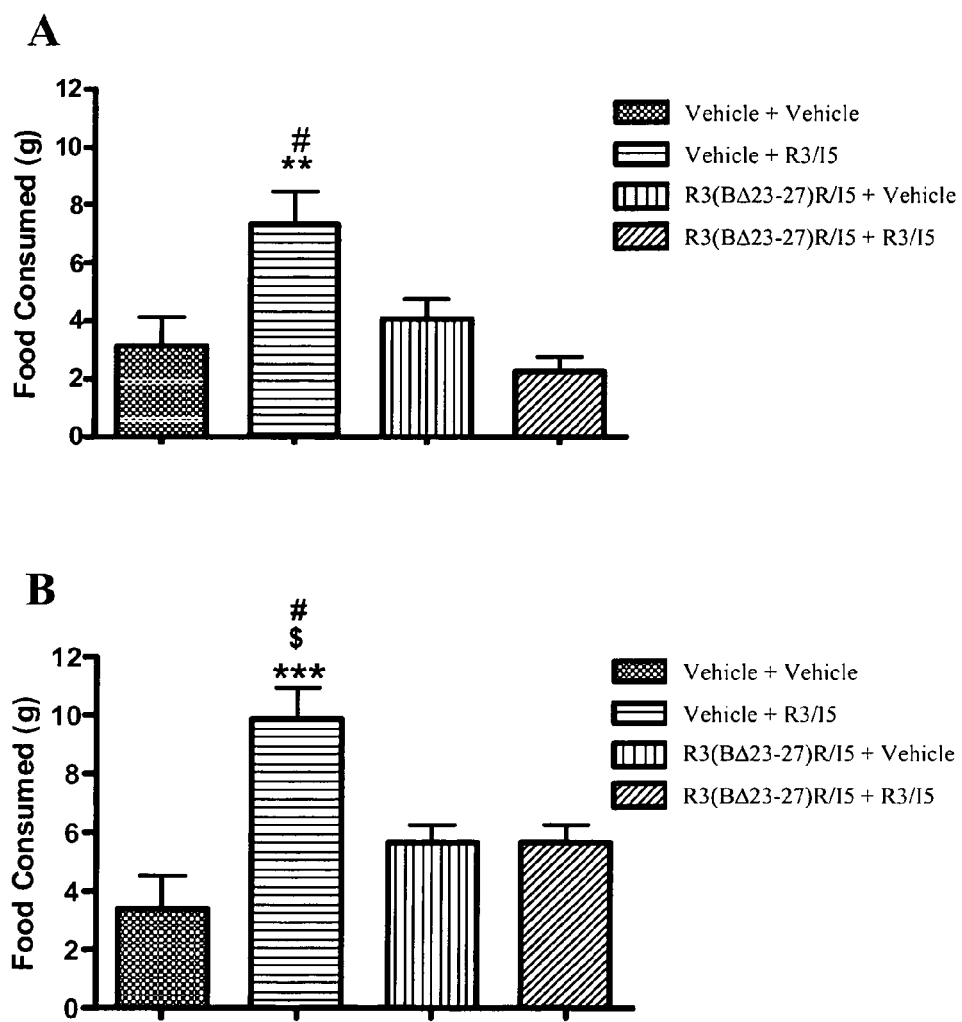
FIG. 6 illustrates food consumption in satiated Wistar rats during the first hour of the test session (i.e., Day 2) following i.c.v. administration of vehicle (5 µL)+vehicle (5 µL), vehicle (5 µl)+R3/I5 (10 µg), R3(BΔ23-27)R/I5 (10 µg)+vehicle (5 µl), and R3(BΔ23-27)R/I5 (10 µg)+R3/I5 (10 µg) (mean±SEM; n=5-6 per group) (A). The figure also shows total food consumption over 4 hours in the same paradigm (B).

As reflected in FIG. 6, intracerebroventricular administration of R3/I5, a selective GPCR135 agonist in the rat (Liu et al., 2005b), stimulated food intake in the above-described paradigm. Prior dosing of R3(BΔ23-27)R/I5 blocked the R3/I5 induced feeding response (FIG. 6). Since the test system described above involved light phase feeding in satiated rats, the lack of significant effect of the antagonist given alone to alter feeding compared to vehicle treated animals is likely due to a lack of feeding drive under these conditions. This result is consistent with earlier reports (McGowan et al., 2005, Hida et al., 2006). By using a selective agonist and by blocking its effect with a selective antagonist, the involvement of GPCR135 in feeding induced by relaxin-3 is demonstrated.

GPCR135 is abundantly expressed in many areas of rodent brain such as the amygdala, superior colliculus, sensory cortex, and olfactory bulb (Sutton et al., 2004; Boels et al., 2004, *Brain Res. De.v Brain Res.*, 152:265-268). The expression of GPCR135 and GPCR135 binding sites are consistent with demonstrated projections of the nucleus incertus (Goto et al., 2001, *J. Com.p Neurol.*, 438:86-122), which is the primary source of relaxin-3 in the rat (Burazin et al., 2002). The overall expression patterns of relaxin-3 and its receptor are consistent with roles in spatial memory, emotional, neuroendocrine, and sensory processing. Recent visualization of relaxin-3 like immunoreactivity in GABA projection neurons of the nucleus incertus is consistent with prior observations and suggests additional actions of relaxin-3, for instance on arousal and locomotor activity (Ma et al., 2007, *Neuroscience*, 144:165-190).

Some expected effects of relaxin-3 have been confirmed in vivo. In addition to expressing relaxin-3 and GPCR135, the nucleus incertus is a prominent source of CRF-R1 expression in the hindbrain (Potter et al., 1994, *Proc. Natl Acad. Sci. USA*, 91:8777-8781). Intracerebroventricular administration of CRF induces relaxin-3 expression in the nucleus incertus, as does a combination of water immersion and restraint stress (Tanaka et al., 2005), suggesting the involvement of relaxin-3 in the stress response.

Although various features and advantages of the invention have been illustrated above, it will be appreciated that the scope of the invention is defined not by the foregoing description, but by the following claims as properly construed under principles of patent law.

What is claimed is:

1. A chimeric polypeptide comprising a B-chain and an A-chain; wherein the B-chain comprises the amino acid sequence RAAPYGVRLCGREFIRAVIFTCR (SEQ ID NO:15) and the A-chain comprises an amino acid sequence selected from the group consisting of the amino acid sequence <EDLQTLCCTDGCSMTDLSALC (SEQ ID NO:19) and the amino acid sequence DVLAGLSSSCCKWGCSKSEISSLC (SEQ ID NO:13), wherein <E represents pyro-Glu.

2. A chimeric polypeptide according to claim 1, wherein the amino acid sequence of the A-chain is <EDLQTLCCTDGCSMTDLSALC (SEQ ID NO:19); wherein <E represents pyro-Glu.

3. A chimeric polypeptide consisting essentially of a B-chain crosslinked to an A-chain; wherein the B-chain comprises the amino acid sequence RAAPYGVRLCGREFIRAVIFTCR (SEQ ID NO:15) and the A-chain comprises an amino acid sequence selected from the group consisting of the amino acid sequence <EDLQTLCCTDGCSMTDLSALC (SEQ ID NO:19) and the amino acid sequence DVLAGLSSSCCKWGCSKSEISSLC (SEQ ID NO:13); wherein <E represents pyro-Glu.

* * * * *

SEQUENCE LISTING

```
<160> NUMBER OF SEQ ID NOS: 28

<210> SEQ ID NO 1
<211> LENGTH: 36
<212> TYPE: DNA
<213> ORGANISM: Artificial Sequence
<220> FEATURE:
<223> OTHER INFORMATION: Primer P1

<400> SEQUENCE: 1
atgctactgc aggccgccat gctgaccgca gcgttg                              36

<210> SEQ ID NO 2
<211> LENGTH: 46
<212> TYPE: DNA
<213> ORGANISM: Artificial Sequence
<220> FEATURE:
<223> OTHER INFORMATION: Primer P2

<400> SEQUENCE: 2
atgataggat ccctagcaaa ggctactgat ttcacttttg ctacac                   46

<210> SEQ ID NO 3
<211> LENGTH: 45
<212> TYPE: DNA
<213> ORGANISM: Artificial Sequence
<220> FEATURE:
<223> OTHER INFORMATION: Primer P3

<400> SEQUENCE: 3
gatgtctgat cgtcttcgtc tgcaggtgaa gatgactgct cggat                    45

<210> SEQ ID NO 4
<211> LENGTH: 45
<212> TYPE: DNA
<213> ORGANISM: Artificial Sequence
<220> FEATURE:
<223> OTHER INFORMATION: Primer P4
```

-continued

<400> SEQUENCE: 4
gtcatcttca cctgcagacg aagacgatca gacatcctgg cccac          45

<210> SEQ ID NO 5
<211> LENGTH: 45
<212> TYPE: DNA
<213> ORGANISM: Artificial Sequence
<220> FEATURE:
<223> OTHER INFORMATION: Primer P5

<400> SEQUENCE: 5
gatgtctgat cgtctccgcc gcccgcaggt gaagatgact gctcg          45

<210> SEQ ID NO 6
<211> LENGTH: 45
<212> TYPE: DNA
<213> ORGANISM: Artificial Sequence
<220> FEATURE:
<223> OTHER INFORMATION: Primer P6

<400> SEQUENCE: 6
tcatcttcac ctgcgggcgg cggagacgat cagacatcct ggccc          45

<210> SEQ ID NO 7
<211> LENGTH: 45
<212> TYPE: DNA
<213> ORGANISM: Artificial Sequence
<220> FEATURE:
<223> OTHER INFORMATION: Primer P7

<400> SEQUENCE: 7
gatgtctgat cgtctccgcc ggccccgca ggtgaagatg actgc           45

<210> SEQ ID NO 8
<211> LENGTH: 45
<212> TYPE: DNA
<213> ORGANISM: Artificial Sequence
<220> FEATURE:
<223> OTHER INFORMATION: Primer P8

<400> SEQUENCE: 8
ttcacctgcg ggggccggcg gagacgatca gacatcctgg cccac          45

<210> SEQ ID NO 9
<211> LENGTH: 42
<212> TYPE: DNA
<213> ORGANISM: Artificial Sequence
<220> FEATURE:
<223> OTHER INFORMATION: Primer P9

<400> SEQUENCE: 9
gtctgatcgt ctccgccggg agccccgca ggtgaagatg ac              42

<210> SEQ ID NO 10
<211> LENGTH: 42
<212> TYPE: DNA
<213> ORGANISM: Artificial Sequence
<220> FEATURE:
<223> OTHER INFORMATION: Primer P10

<400> SEQUENCE: 10
cctgcggggg ctcccggcgg agacgatcag acatcctggc cc             42

<210> SEQ ID NO 11
<211> LENGTH: 40
<212> TYPE: DNA

```
<213> ORGANISM: Artificial Sequence
<220> FEATURE:
<223> OTHER INFORMATION: Primer Pi5

<400> SEQUENCE: 11
actagaggat ccttagcaaa gagcactcaa atcagtcatg                    40

<210> SEQ ID NO 12
<211> LENGTH: 27
<212> TYPE: PRT
<213> ORGANISM: Homo Sapiens

<400> SEQUENCE: 12

Arg Ala Ala Pro Tyr Gly Val Arg Leu Cys Gly Arg Glu Phe Ile Arg
1               5                   10                  15

Ala Val Ile Phe Thr Cys Gly Gly Ser Arg Trp
            20                  25

<210> SEQ ID NO 13
<211> LENGTH: 24
<212> TYPE: PRT
<213> ORGANISM: Homo Sapiens

<400> SEQUENCE: 13

Asp Val Leu Ala Gly Leu Ser Ser Ser Cys Cys Lys Trp Gly Cys Ser
1               5                   10                  15

Lys Ser Glu Ile Ser Ser Leu Cys
            20

<210> SEQ ID NO 14
<211> LENGTH: 22
<212> TYPE: PRT
<213> ORGANISM: Artificial Sequence
<220> FEATURE:
<223> OTHER INFORMATION: R3(Bdel23-27) B-chain

<400> SEQUENCE: 14

Arg Ala Ala Pro Tyr Gly Val Arg Leu Cys Gly Arg Glu Phe Ile Arg
1               5                   10                  15

Ala Val Ile Phe Thr Cys
            20

<210> SEQ ID NO 15
<211> LENGTH: 23
<212> TYPE: PRT
<213> ORGANISM: Artificial Sequence
<220> FEATURE:
<223> OTHER INFORMATION: R3(Bdel23-27)R B-chain

<400> SEQUENCE: 15

Arg Ala Ala Pro Tyr Gly Val Arg Leu Cys Gly Arg Glu Phe Ile Arg
1               5                   10                  15

Ala Val Ile Phe Thr Cys Arg
            20

<210> SEQ ID NO 16
<211> LENGTH: 23
<212> TYPE: PRT
<213> ORGANISM: Artificial Sequence
<220> FEATURE:
<223> OTHER INFORMATION: R3(Bdel24-27) B-chain

<400> SEQUENCE: 16

Arg Ala Ala Pro Tyr Gly Val Arg Leu Cys Gly Arg Glu Phe Ile Arg
1               5                   10                  15
```

```
Ala Val Ile Phe Thr Cys Gly
            20

<210> SEQ ID NO 17
<211> LENGTH: 24
<212> TYPE: PRT
<213> ORGANISM: Artificial Sequence
<220> FEATURE:
<223> OTHER INFORMATION: R3(Bdel25-27) B-chain

<400> SEQUENCE: 17

Arg Ala Ala Pro Tyr Gly Val Arg Leu Cys Gly Arg Glu Phe Ile Arg
1               5                   10                  15

Ala Val Ile Phe Thr Cys Gly Gly
            20

<210> SEQ ID NO 18
<211> LENGTH: 25
<212> TYPE: PRT
<213> ORGANISM: Artificial Sequence
<220> FEATURE:
<223> OTHER INFORMATION: R3(Bdel26-27) B-chain

<400> SEQUENCE: 18

Arg Ala Ala Pro Tyr Gly Val Arg Leu Cys Gly Arg Glu Phe Ile Arg
1               5                   10                  15

Ala Val Ile Phe Thr Cys Gly Gly Ser
            20                  25

<210> SEQ ID NO 19
<211> LENGTH: 21
<212> TYPE: PRT
<213> ORGANISM: Artificial Sequence
<220> FEATURE:
<223> OTHER INFORMATION: INSL5 A-chain

<400> SEQUENCE: 19

Glu Asp Leu Gln Thr Leu Cys Cys Thr Asp Gly Cys Ser Met Thr Asp
1               5                   10                  15

Leu Ser Ala Leu Cys
            20

<210> SEQ ID NO 20
<211> LENGTH: 28
<212> TYPE: PRT
<213> ORGANISM: Homo Sapiens

<400> SEQUENCE: 20

Lys Trp Lys Asp Asp Val Ile Lys Leu Cys Gly Arg Glu Leu Val Arg
1               5                   10                  15

Ala Gln Ile Ala Ile Cys Gly Met Ser Thr Trp Ser
            20                  25

<210> SEQ ID NO 21
<211> LENGTH: 29
<212> TYPE: PRT
<213> ORGANISM: Homo Sapiens

<400> SEQUENCE: 21

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser
            20                  25
```

<210> SEQ ID NO 22
<211> LENGTH: 31
<212> TYPE: PRT
<213> ORGANISM: Homo Sapiens

<400> SEQUENCE: 22

Pro Thr Pro Glu Met Arg Glu Lys Leu Cys Gly His His Phe Val Arg
1               5                   10                  15

Ala Leu Val Arg Val Cys Gly Gly Pro Arg Trp Ser Thr Glu Ala
            20                  25                  30

<210> SEQ ID NO 23
<211> LENGTH: 27
<212> TYPE: PRT
<213> ORGANISM: Homo Sapiens

<400> SEQUENCE: 23

Glu Ser Leu Ala Ala Glu Leu Arg Gly Cys Gly Pro Arg Phe Gly Lys
1               5                   10                  15

His Leu Leu Ser Tyr Cys Pro Met Pro Glu Lys
            20                  25

<210> SEQ ID NO 24
<211> LENGTH: 24
<212> TYPE: PRT
<213> ORGANISM: Homo Sapiens

<400> SEQUENCE: 24

Lys Glu Ser Val Arg Leu Cys Gly Leu Glu Tyr Ile Arg Thr Val Ile
1               5                   10                  15

Tyr Ile Cys Ala Ser Ser Arg Trp
            20

<210> SEQ ID NO 25
<211> LENGTH: 28
<212> TYPE: PRT
<213> ORGANISM: Homo Sapiens

<400> SEQUENCE: 25

Ile Ser Ser Ala Arg Lys Leu Cys Gly Arg Tyr Leu Val Lys Glu Ile
1               5                   10                  15

Glu Lys Leu Cys Gly His Ala Asn Trp Ser Gln Phe
            20                  25

<210> SEQ ID NO 26
<211> LENGTH: 30
<212> TYPE: PRT
<213> ORGANISM: Homo Sapiens

<400> SEQUENCE: 26

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 27
<211> LENGTH: 32
<212> TYPE: PRT
<213> ORGANISM: Homo Sapiens

<400> SEQUENCE: 27

Gly Pro Glu Thr Leu Cys Gly Ala Glu Leu Val Asp Ala Leu Gln Phe
1               5                   10                  15

```
Val Cys Gly Asp Arg Gly Phe Tyr Phe Asn Lys Pro Thr Gly Tyr Gly
            20                  25                  30

<210> SEQ ID NO 28
<211> LENGTH: 31
<212> TYPE: PRT
<213> ORGANISM: Homo Sapiens

<400> SEQUENCE: 28

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro
            20                  25                  30
```